United States Patent [19]

Vecchietti et al.

[11] Patent Number: 4,528,296

[45] Date of Patent: Jul. 9, 1985

[54] DERIVATIVES OF AMINOPYRIDINECARBOXYLIC ACIDS AND PHARMACEUTICAL COMPOSITIONS CONTAINING THEM

[75] Inventors: Vittorio Vecchietti; Giorgio Ferrari, both of Milan; Cesare Casagrande, Arese, all of Italy

[73] Assignee: Simes, Societa Italiana Medicinalle Sintetici, Milan, Italy

[21] Appl. No.: 557,584

[22] Filed: Dec. 2, 1983

[30] Foreign Application Priority Data

Dec. 3, 1982 [IT] Italy ........................ 24576 A/82

[51] Int. Cl.$^3$ ............... C07D 213/80; C07D 213/79; C07D 213/75; A61K 31/455
[52] U.S. Cl. ................................. 514/346; 546/297; 546/309; 546/291; 514/352
[58] Field of Search ............ 546/297, 309, 291; 424/266

[56] References Cited

U.S. PATENT DOCUMENTS 3,415,835  12/1968  Stempel ..................... 260/295.5

FOREIGN PATENT DOCUMENTS 2756771  6/1978  Fed. Rep. of Germany.
2946909  6/1981  Fed. Rep. of Germany.
2018248  10/1979  United Kingdom.
2054586  2/1981  United Kingdom.

OTHER PUBLICATIONS

Merck Index, Tenth Edition, (1983), p. 244.
Wagner, G. et al., "Inhibitors of a Rat Brain Enkephalin Aminopeptidase", Journal of Neurochemistry, 37, (3), Sep. 1981, pp. 709–713.

Primary Examiner—Henry R. Jiles
Assistant Examiner—Dale A. Bjorkman
Attorney, Agent, or Firm—Cushman, Darby & Cushman

[57] ABSTRACT

Derivatives of aminopyridinecarboxylic acids which inhibit the dipeptidyl carboxy peptidase (DPCP), methods for their preparation and pharmaceutical compositions containing them.

The compounds have formula:

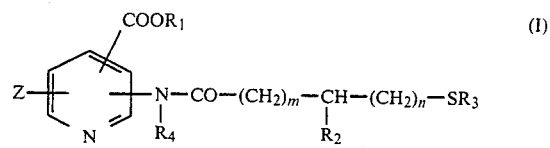

where
Z is hydrogen, alkyl having from 1 to 3 carbon atoms, halogen or alkoxy having from 1 to 3 carbon atoms;
R1 is hydrogen, alkyl having from 1 to 6 carbon atoms, arylalkyl having from 7 to 12 carbon atoms, aryl having from 6 to 15 carbon atoms;
m and n are an integer of from 0 to 4 each provided, however, the m+n is lower than 5;
R2 is hydrogen, alkyl having from 1 to 6 carbon atoms or arylalkyl having from 7 to 12 carbon atoms;
R3 is hydrogen or acyl having from 1 to 8 carbon atoms;
R4 is hydrogen or alkyl having from 1 to 3 carbon atoms;

and their pharmaceutically acceptable salts with organic or inorganic acids.

12 Claims, No Drawings

DERIVATIVES OF AMINOPYRIDINECARBOXYLIC ACIDS AND PHARMACEUTICAL COMPOSITIONS CONTAINING THEM

This invention relates to new derivatives of aminopyridinecarboxylic acids which inhibit the dipeptidyl carboxy peptidase (DPCP), methods for their preparation and pharmaceutical compositions containing them.

More particularly this invention relates to the products having formula

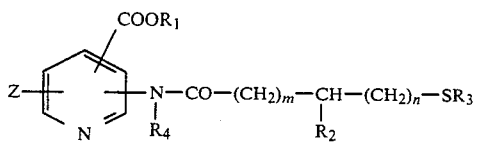
(I)

where
Z is hydrogen, alkyl having from 1 to 3 carbon atoms, halogen or alkoxy having from 1 to 3 carbon atoms;
$R_1$ is hydrogen, alkyl having from 1 to 6 carbon atoms, arylalkyl having from 7 to 12 carbon atoms, aryl having from 6 to 15 carbon atoms;
m and n are an integer of from 0 to 4 each provided, however, that m+n is lower than 5;
$R_2$ is hydrogen, alkyl having from 1 to 6 carbon atoms or arylalkyl having from 7 to 12 carbon atoms;
$R_3$ is hydrogen or acyl having from 1 to 8 carbon atoms;
$R_4$ is hydrogen or alkyl having from 1 to 3 carbon atoms;
and their pharmaceutically acceptable salts with organic or inorganic acids.

The new derivatives of this invention can be prepared according to many acylation techniques, more particularly those developed for the synthesis of the peptidic bonds, by reacting a compound of formula:

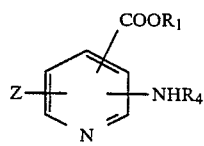
(II)

where Z, $R_1$ and $R_4$ have the above mentioned meanings; or a reactive derivative thereof, with a compound of formula:

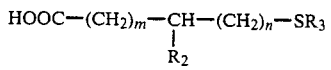
(III)

where m, n, $R_2$ and $R_3$ have the above mentioned meanings; or a reactive derivative thereof.

Examples of useful reactive derivatives of the compounds of formula (III) are the symmetrical anhydrides, the mixed anhydrides and the halides.

Also the possible protection or deprotection of either carboxy or thiol groups which are not involved in the condensation reaction are carried out by those techniques which are usually employed in the peptide chemistry.

When it is not used a reactive derivative, the reaction between the compounds of formula (II) and (III), is carried out by usual techniques in the presence of suitable condensing agent such as N,N-dicyclohexylcarbodiimide alone or together with N-hydroxysuccinimide, N-hydroxybenzotriazole, pentachlorophenol, alpha-chlorovinyl-ethylether, ethoxyacetylene, cyanamide, ketenimines, ketenes, triphenylphosphite or imidazole.

This reaction is preferably carried out in the presence of a suitable diluent such as tetrahydrofuran, dimethoxyethane, N,N-dimethylformamide, methylene chloride or acetonitrile at a temperature of from $-30°$ C. and the boiling temperature of the reaction mixture.

Also the reaction between a reactive derivative of a compound of formula (III) and a compound of formula (II) is carried out by usual techniques.

Examples of reactive derivatives of compounds of formula (III) are the acyl halides, the mixed or symmetrical anhydrides, the esters of hydroxy compounds such as N-hydroxysuccinimide, N-hydroxybenzotriazole, pentachlorophenol and 2,4-dinitrophenol. The reaction can be carried out also in the presence of a catalizer such as 4-N,N-dimethylaminopyridine or 4-pyrrolidinepyridine.

This reaction is preferably carried out in the presence of a suitable diluent such as tetrahydrofuran, dimethoxyethane, N,N-dimethylformamide or acetonitrile at a temperature of from $-30°$ C. and the boiling temperature of the reaction mixture.

When $R_2$ is not hydrogen the compounds of formula (III) are optically active, therefor, it is an object of this invention both the single R and S forms of compounds of formula (I) and their racemic mixture.

A preferred method for preparing the optically active compounds of formula (I) contemplates the use, as starting materials, of the corresponding optically active compounds of formula (III). Alternatively, it is prepared the racemate of formula (I) which is then resolved into the single optical isomers by usual techniques.

Also the pharmaceutically acceptable salts of compounds (I) are prepared by usual techniques.

Preferred compounds of this invention are those of formula (I) where Z is hydrogen, $R_1$ is alkyl having from 1 to 3 carbon atoms, $R_2$ is H, methyl or benzyl, $R_3$ is acetyl or benzoyl, $R_4$ is H or methyl, m is 0 and n is 1.

The compounds of formula (I) are active as inhibitors of the DPCP involved in the metabolic deactivation of enkephalins (enkephalinase); this activity has proved to be very specific because compounds (I) have proved to be non-active as inhibitors of other peptidases such as amino peptidase.

Because of their activity as DPCP inhibitors the compounds of this invention are useful as analgesic agents, anti-hypertensives as well as for treating drug addition and psychic disorders.

The evaluation of the inhibitory effect on enkephalinase and on aminopeptidase activity respectively has been made as follows:

(a) enkephalinase: it has been used the enzymatic preparation extracted from the particulate fraction of striata of rats purified on discontinous gradient of sucrose (Blumberg et al., Life Sci., 28, (1981), 301); the evaluation of the enzymatic activity has been made using $^3$H-Tyr-Leucine-Enkephalin as substrate (Vogel and Alstein, FEBS Lett., 80, (1977), 332).

(b) amino peptidase: as enzyme source it has been used the soluble fraction of point (a) above and $^3$H-Tyr-Leucine-Enkephalin as substrate (Vogel and Alstein, FEBS Lett., 80, (1977), 332).

The results are shown in the following

TABLE 1

| Drug concentration which inhibits 50% of the enzymatic activities (IC50(M)) | | |
|---|---|---|
| Compound (Example No.) | Enkephalinase | Amino Peptidase |
| 8 | $5 \times 10^{-7}$ | $>10^{-6}$ |
| 31 | $5 \times 10^{-7}$ | $>10^{-6}$ |
| 23 | $2 \times 10^{-7}$ | $>10^{-6}$ |
| 14 | $5 \times 10^{-8}$ | $>10^{-6}$ |
| 18a | $3 \times 10^{-7}$ | $>10^{-6}$ |
| 13 | $2 \times 10^{-7}$ | $>10^{-6}$ |
| 17 | $1 \times 10^{-7}$ | $>10^{-6}$ |
| 16 | $7 \times 10^{-7}$ | $>10^{-6}$ |
| 28 | $1.8 \times 10^{-9}$ | $>10^{-6}$ |
| Captopril | $>10^{-6}$ | $>10^{-6}$ |
| Bestatin | $>10^{-6}$ | $2 \times 10^{-7}$ |

The inhibitory activity on enkephalinase has been evaluated "in vivo" by monitoring the potentiation of the analgesic effect induced in mice by Methionine-Enkephalin (Met-Enk) intracerebrally administered using the hot plate test (Eddy et al., J. Pharmacol., 98, (1950), 121). The intracerebral (IC) administration has been made according to Haley and McCormick (Brit. J. Pharmacol., 12, (1957), 12). The results are shown in the following

TABLE 2

| Effect on Met—Enk analgesia in mice | | |
|---|---|---|
| Compound (Example No) | Dose μg/ic | Latency Time $X \pm SE$ (sec) |
|  | — | $10.7 \pm 0.8$ |
| Met—Enk | 50 | $14.7 \pm 1.3$ |
| Met—Enk + 8 | 50 + 12,5 | $19.6 \pm 2.1^*$ |
| Met—Enk + 31 | 50 + 12,5 | $15.4 \pm 1.2$ |
| Met—Enk + 23 | 50 + 25 | $26.1 \pm 2.1^*$ |
| Met—Enk + 14 | 50 + 25 | $27.7 \pm 1.5^*$ |
| Met—Enk + 18a | 50 + 50 | $13.1 \pm 0.9$ |
| Met—Enk + 17 | 50 + 50 | $13.8 \pm 1.4$ |
| Met—Enk + 16 | 50 + 5 | $14.8 \pm 1.1$ |
| Met—Enk + 28 | 50 + 50 | $27.0 \pm 1.6^*$ |

*P 0,05 with respect to the group treated with Met—Enk alone ("t" test)

The acute toxicity of compounds of this invention has been evaluated after oral administration in mice

TABLE 3

| Acute toxicity in mice after oral administration (mg/kg) | | |
|---|---|---|
| Compound (Example No.) | LD50 (mg/kg) | Confidence limits (95%) |
| 24 | 390 | (361–421) |
| 25 | 329 | (244–444) |
| 26 | 421 | (369–480) |

This invention relate also to pharmaceutical compositions containing as active ingredient a compound of formula (I) or a pharmaceutically acceptable salt thereof.

These compositions may contain the active ingredient together with organic or inorganic, liquid or solid pharmaceutical carriers and may be administered by oral, parenteral or rectal route.

The pharmaceutical compositions of this invention will contain a quantity of a compound of formula (I) sufficient to induce inhibitory effect on enkephalinase.

Preferably, the compositions will contain the active ingredient in an active but nontoxic amount selected from 30 mg to 300 mg of active ingredient calculated as the base per dosage unit.

The daily dosage regimen is selected with the conditions known to be factors in the art, for example, the age and the weight of the subject, the severity of the clinical disorder, the route of administration and the relative potency of the active ingredient compared to the activity of Captopril (1,-(3-mercapto-2-methyl-1-oxopropyl)-L-proline) and Bestatin ([2S,3R)-3-amino-2-hydroxy-4-phenylbutanoyl]-L-leucine) in the test systems described hereinbefore.

Preferably the daily dosage, based on total quantities of the base, is from 60 mg to 1 g per day, administered preferably as 30–300 mg of base per dosage unit which is administered from 1 to 5 times per day.

The finished pharmaceutical forms may be solid such as tablets, sugar coated pills, capsules, powders, granules or liquid such as solutions, suspensions or emulsions.

They may be prepared in such a way that the release of the drug after administration is time sustained.

In addition to the carriers they may contain preserving, stabilizing, wetting, emulsifying agents, salts for the regulation of the osmotic pressure, buffers, colouring agents, flavouring agents. They can be prepared by known methods and can contain also other therapeutic agents.

The following examples illustrate this invention without limiting it.

EXAMPLE 1

A solution of 7.6 g (50 mmol) of methyl 2-aminonicotinate, 8.9 g (55 mmol) of 2-acetylthiomethyl-propionic acid, 12.4 (60 mmol) of N,N-dicyclohexylcarbodiimide in 150 ml of dried methylene chloride is refluxed for ten hours. After evaporation to dryness in vacuo, the residue is taken up with 100 ml of petroleum ether/ethyl acetate 7:3 and filtered to remove the insoluble dicyclohexylurea.

The filtrate is evaporated in vacuo and purified by chromatography on a silica gel column eluting with petroleum ether/ethyl acetate 8:2.

Methyl 2-(2-acetylthiomethyl-propionamido)-nicotinate is thus obtained (yield, 71%) as a chromatographically pure oil (thin layer chromatography on silica gel, eluent: toluene/ethyl acetate; U.V. detection, $I_2$; mass spectrum: $M^+$ at 296 m/e).

EXAMPLE 2

4 g (13.5 mmol) of methyl 2-(2-acetylthiomethyl-propionamido)-nicotinate obtained as disclosed in Example 1 are dissolved into 100 ml of 50% aqueous methanol under nitrogen, to this solution are added 2.73 g (27 mmol) of triethylamine and the reaction mixture is stirred for two hours at room temperature. The reaction mixture is made acid and then evaporated in vacuo; the residue is purified by chromatography on a silica gel column eluting with methylene chloride: methyl 2-(2-mercaptomethyl-propionamido)-nicotinate (m.p. 50°–52° C., from petroleum ether; yield, 29%) is thus obtained.

EXAMPLE 3

A solution of 4 g (13.5 mmol) of methyl 2-(2-acetylthiomethyl-propionamido)-nicotinate obtained as disclosed in Example 1, 1.62 g (40.5 mmol) of sodium hydroxide in 20 ml of water and 100 ml of methanol is stirred under nitrogen at room temperature for two hours. After acidification to pH 4 with hydrochloric acid and evaporation of methanol in vacuo, the residue is diluted with 70 ml of water and extracted with chloroform/methanol 7:3. The extract is dried over sodium sulfate, filtered and evaporated. The residue is crystallized from acetone/petroleum ether to give 2-(2-mercaptothiomethyl-propionamido)-nicotinic acid; m.p. 95°–100° C.; Yield, 40%.

EXAMPLE 4

Following the procedure of Example 1, but substituting an equivalent amount of methyl 4-amino-nicotinate for methyl 2-amino-nicotinate and using methylene chloride as eluent for the column chromatography, methyl 4-(2-acetylthiomethyl-propionamido)-nicotinate is obtained; m.p. 55°–57° C., from petroleum ether.

EXAMPLE 5

Following the procedure of Example 2, but substituting an equivalent amount of methyl 4-(2-acetylthiomethyl-propionamido)-nicotinate, obtained as disclosed in Example 4, for methyl 2-(2-acetylthiomethyl-propionamido)-nicotinate, methyl 4-(2-mercaptomethyl-propionamido)-nicotinate is obtained, m.p. 54°–56° C., from petroleum ether.

EXAMPLE 6

Following the procedure of Example 1, but substituting an equivalent amount of ethyl 6-amino-nicotinate for methyl 2-amino-nicotinate, using pyridine as reaction solvent and maintaining the reaction mixture at 50°–60° C. for 5 hours; ethyl 6-(2-acetylthiomethyl-propionamido)-nicotinate is obtained which yields the corresponding hydrochloride salt with an ethereal solution of hydrochloric acid; m.p. 176°–178° C., from ethyl alcohol.

EXAMPLE 7

Following the procedure of Example 2, but substituting an equivalent amount of ethyl 6-(2-acetylthiomethyl-propionamido)-nicotinate, obtained as disclosed in Example 6, for methyl 2-(2-acetylthiomethyl-propionamido)-nicotinate, ethyl 6-(2-mercaptomethyl-propionamido)-nicotinate is obtained; m.p. 58°–61° C. from petroleum ether.

EXAMPLE 8

Following the procedure of Example 3, but substituting an equivalent amount of ethyl 6-(2-acetylthiomethyl-propionamido)-nicotinate, obtained as disclosed in Example 6, for methyl 2-(2-acetylthiomethyl-propionamido)-nicotinate, 6-(2-mercaptomethyl-propionamido)-nicotinic acid is prepared; m.p. 220°–222° C., from absolute ethanol.

EXAMPLE 9

A solution of 5 g (33 mmol) of methyl 6-amino-picolinate and 6.55 g (36.3 mmol) of 2-acetylthiomethyl-propionyl chloride in 50 ml of pyridine is stirred for one hour.

The reaction mixture is poured into water and extracted with ethyl acetate, the extract is washed with water, dried over sodium sulfate and evaporated; the residue is taken up with ethyl acetate/petroleum ether to afford methyl 6-(2-acetylthiomethyl-propionamido)-picolinate; m.p. 75°–77° C.; yield, 84%.

EXAMPLE 10

Following the procedure of Example 2, but substituting an equivalent amount of methyl 6-(2-acetylthiomethyl-propionamido)-picolinate, obtained as disclosed in Example 9, for methyl 2-(2-acetylthiomethyl-propionamido)-nicotinate, methyl 6-(2-mercaptomethyl-propionamido)-picolinate is obtained as a chromatographically pure oil (thin layer chromatography on silica gel, eluent: methylene chloride/toluene/methanol 25:5:3; U.V. detection, $I_2$; mass spectrum: M+ at 254 m/e).

EXAMPLE 11

Following the procedure of Example 3, but substituting an equivalent amount of methyl 6-(2-acetylthiomethyl-propionamido)-picolinate, obtained as disclosed in Example 9, for methyl 2-(2-acetylthiomethyl-propionamido)-nicotinate, 6-(2-mercaptomethyl-propionamido)-picolinic acid is obtained; m.p. 178°–179° C., from acetone/ethyl acetate.

EXAMPLE 12

Following the procedure of Example 1, but substituting an equivalent amount of methyl 5-amino-nicotinate for methyl 2-amino-nicotinate, using pyridine as solvent and maintaining the reaction mixture at room temperature for seven hours, methyl 5-(2-acetylthiomethyl-propionamido)-nicotinate is obtained; m.p. 88°–90° C., from ethyl acetate.

EXAMPLE 13

Following the procedure of Example 2, but substituting an equivalent amount of methyl 5-(2-acetylthiomethyl-propionamido)-nicotinate, obtained as disclosed in Example 12, for methyl 2-(2-acetylthiomethyl-propionamido)-nicotinate and using a mixture of methylene chloride/methanol 99:1 as eluent for the chromatographic column, methyl 5-(2-mercaptomethyl-propionamido)-nicotinate is obtained: m.p. 96°–97° C., from ethyl acetate.

EXAMPLE 14

Following the procedure of Example 3, but substituting an equivalent amount of methyl 5-(2-acetylthiomethyl-propionamido)-nicotinate, obtained as disclosed in Example 12, for methyl 2-(2-acetylthiomethyl-propionamido)-nicotinate and substituting an equivalent amount of potassium carbonate for sodium hydroxide and maintaining the reaction mixture under stirring for six hours at room temperature, 5-(2-mercaptomethyl-propionamido)-nicotinic acid is obtained after purification on a silica gel column (eluent methylene chloride/methanol 99:1); m.p. 160°–165° C., from acetone.

EXAMPLE 15

Following the procedure of Example 9, but substituting an equivalent amount of 5-amino-nicotinic acid for methyl 6-amino-picolinate and prolonging the reaction time to four hours, 5-(2-acetylthiomethyl-propionamido)-nicotinic acid is obtained; m.p. 154°–158° C., from ethyl acetate.

EXAMPLE 16

To a solution of 4 g (24 mmol) of methyl 5-methylamino-nicotinate and 0.29 g (2.4 mmol) of 4-dimethylaminopyridine in 50 ml of pyridine are added, at room temperature and under stirring, 5,2 g (28.8 mmol) of 2-methyl-3-thioacetyl-propionic acid chloride. After one hour the reaction mixture is poured into water and extracted with ethyl acetate; the combined organic phase is dried over sodium sulfate and evaporated in vacuo and the residue is crystallized from ethyl acetate to afford methyl 5-(2-acetylthiomethyl-N-methyl-propionamido)-nicotinate; m.p. 123°–125° C.; Yield, 90%.

The intermediate methyl 5-methylamino-nicotinate has been obtained as follows: reaction of methylamine (40% in water) with 5-bromo-nicotinic acid in autoclave at 140° C. for seven hours gives 5-methylamino-nicotinic acid, m.p. 239°–242° C. from ethanol/water; this acid reacts with SOCl in methanol under reflux for seven hours to afford the ester (methyl 5-methylaminonicotinate; m.p. 113°–115° C., from petroleum ether.

EXAMPLE 17

Following the procedure of Example 3, but substituting an equivalent amount of methyl 5-(2-acetylthiomethyl-N-methyl-propionamido)-nicotinate, obtained as disclosed in Example 16, for methyl 2-(2-acetylthiomethyl-propionamido)-nicotinate, 5-(2-mercaptomethyl-N-methyl-propionamido)-nicotinic acid is obtained; m.p. 190°–192° C., from methanol.

EXAMPLE 18

(a)

0.98 g (8.95 mmol) of ethyl chloroformate have been added at −12° C. under nitrogen to a solution of 2 g (8.95 mmol) of S(−)-2-benzoylthiomethyl propanoic acid and 0.9 g (8.95 mmol) of triethylamine in 40 ml of N,N-dimethylformamide. After two minutes at −12° C., 1.23 g (8.95 mmol) of 5-amino-nicotinic acid are added; after further three hours at room temperature, the reaction mixture is poured into water and extracted with ethyl acetate. The combined organic phase is washed with water, dried over sodium sulfate, evaporated to dryness in vacuo.

The thus obtained residue is purified by chromatography on silica gel column eluting with methylene chloride/methanol 95:5. The thus separated product is crystallized from acetone; S(−)-5-(2-benzoylthiomethyl-propionamido)-nicotinic acid is thus obtained; yield, 49%; m.p. 213°–215° C.; $[\alpha]_D^{20} = -153°$ (c=1, 95% methanol).

(b)

Following the same procedure but using R(+)-2-benzoylthiomethyl-propionic acid it is obtained the corresponding enantiomer: R(+)-5-(2-benzoylthiomethyl-propionamido)-nicotinic acid.

(c)

The corresponding racemate has been obtained in analogous manner starting from (±)-2-benzoylthiomethylpropionic acid; m.p. 202°–204° C. (from acetone).

EXAMPLE 19

(a)

Following the procedure of Example 18a, but substituting an equivalent amount of methyl 5-amino-nicotinate for 5-amino-nicotinic acid, methyl; S(−)-5-(2-benzoylthiomethyl-propionamido)-nicotinate; m.p. 140°–142° C., from acetonitrile; $[\alpha]_D^{20} - 186.3°$ (c=1, 95% methanol).

(b)

Following the procedure of Example 18b, but substituting an equivalent amount of methyl 5-amino-nicotinate for 5-amino-nicotinic acid it is obtained the corresponding dextrorotatory enantiomer.

EXAMPLE 20

(a)

Following the procedure of Example 3, but substituting an equivalent amount of methyl S(−)-5-(2-benzoylthiomethyl-propionamido)-nicotinate, obtained as disclosed in Example 19, for methyl 2-(2-acetylthiomethyl-propionamido)-nicotinate, S(−)-5-(2-mercaptomethyl-propionamido)-nicotinic acid is obtained; m.p. 232°–233° C., from ethanol/ethyl acetate; $[\alpha]_D^{20} - 69.27°$ (c=1, 95% ethanol).

(b)

By working in analogous manner and starting from methyl R(+)-5-(2-mercaptomethyl-propionamido)-nicotinate it is obtained the corresponding dextrorotatory enantiomer.

(c)

The corresponding racemate can be obtained as disclosed in Example 19 or following the above mentioned procedure and starting from methyl (±)-5-(2-benzoylthiomethyl-propionamido)-nicotinate.

EXAMPLE 21

Following the procedure of Example 1, but substituting an equivalent amount of methyl 5-amino-picolinate for methyl 2-amino-nicotinate and using pyridine as solvent, maintaining the reaction mixture at 40° C. for seven hours, using methylene chloride as eluent for the chromatography column, methyl 5-(2-acetylthiomethyl-propionamido)-picolinate; m.p. 169°–171° C., from ethyl acetate.

EXAMPLE 22

Following the procedure of Example 2, but substituting an equivalent amount of methyl 5-(2-acetylthiomethyl-propionamido)-picolinate, obtained as disclosed in Example 21, for methyl 2-(2-acetylthiomethyl-propionamido)-nicoticate, methyl 5-(2-mercaptomethyl-propionamido)-picolinate; m.p. 140°–142° C., from ethyl acetate.

EXAMPLE 23

Following the procedure of Example 3, but substituting an equivalent amount of methyl 5-(2-acetylthiomethyl-propionamido)-picolinate, obtained as disclosed in Example 21, for methyl 2-(2-acetylthiomethyl-propionamido)-nicotinate, 5-(2-mercaptomethyl-propionamido)-picolinic acid is obtained; m.p. 175°–177° C., from acetone.

EXAMPLE 24

Following the procedure of Example 1, but substituting an equivalent amount of methyl 3-amino-picolinate for methyl 2-amino-nicotinate, using hexamethylphosphoramide as solvent and maintaining the reaction mixture at 60° C. for 8 hours, methyl 3-(2-acetylthiomethyl-propionamido)-picolinate is obtained; m.p. 54°-56° C., from ethyl ether/petroleum ether.

EXAMPLE 25

Following the procedure of Example 2, but substituting an equivalent amount of methyl 3-(2-acetylthiomethyl-propionamido)-picolinate, obtained as disclosed in Example 24, for methyl 2-(2-acetylthiomethyl-propionamido)-nicotinate and using ethyl acetate as eluent for the chromatography column, methyl 3-(2-mercaptomethyl-propionamido)-picolinate is obtained; m.p. 55°-56° C., from petroleum ether.

EXAMPLE 26

Following the procedure of Example 3, but substituting an equivalent amount of methyl 3-(2-acetylthiomethyl-propionamido)-picolinate, obtained as disclosed in Example 24, for methyl 2-(2-acetylthiomethyl-propionamido)-nicotinate 2-(2-acetylthiomethyl-propionamido)-picolinic acid is obtained; m.p. 162°-164° C., from acetone.

EXAMPLE 27

Following the procedure of Example 1, but substituting an equivalent amount of methyl 2-amino-isonicotinate and 2-acetylthiomethyl-3-phenyl-propionic acid respectively for methyl 2-amino-nicotinate and 2-acetylthiomethyl-3-phenyl-propionic acid, using pyridine as reaction solvent, maintaining the reaction mixture at 50°-60° C. for five hours and purifying by chromatography on silica gel column (eluent, petroleum ether/ether 7:3), methyl 2-(2-acetylthiomethyl-3-phenyl-propionamido)-isonicotinate is obtained as an oil which is transformed into the corresponding hydrochloride with an alcoholic solution of hydrogen chloride; m.p. 137°-139° C., from acetone/ether.

EXAMPLE 28

Following the procedure of Example 3, but substituting an equivalent amount of methyl 2-(2-acetylthiomethyl-3-phenyl-propionamido)-isonicotinate, obtained as disclosed in Example 27, for methyl 2-(2-acetylthiomethyl-propionamido)-nicotinate and purifying by chromatography on silica gel column, eluting with methylene chloride/methanol 95:5; 2-(2-mercaptomethyl-3-phenyl-propionamido)-isonicotinic acid is obtained; m.p. 234°-236° C., from absolute ethanol.

EXAMPLE 29

Following the procedure of Example 1, but substituting an equivalent amount of methyl 2-amino-isonicotinate for methyl 2-amino-nicotinate, using pyridine as reaction solvent, maintaining the reaction mixture at 50°-60° C. for five hours, methyl 2-(2-acetylthiomethyl-propionamido)-isonicotinate is obtained; m.p. 105°-106° C., from ethyl acetate.

EXAMPLE 30

Following the procedure of Example 2, but substituting an equivalent amount of methyl 2-(2-acetylthiomethyl-propionamido)-isonicotinate, obtained as disclosed in Example 29, for methyl 2-(2-acetylthiomethyl-propionamido)-nicotinate and using methylene chloride/methanol 99:1 as eluent for the chromatography column, methyl 2-(2-mercaptomethyl-propionamido)-isonicotinate which is transformed into the corresponding hydrochloride with an ethereal solution of hydrogen chloride; m.p. 90°-95° C., from acetone/ethyl ether.

EXAMPLE 31

Following the procedure of Example 3, but substituting an equivalent amount of methyl 2-(2-acetylthiomethyl-propionamido)-isonicotinate, obtained as disclosed in Example 29, for methyl 2-(2-acetylthiomethyl-propionamido)-nicotinate; 2-(2-mercaptomethyl-propionamido)-isonicotinic acid is obtained; m.p. 247°-248° C., from ethanol/water.

We claim:

1. A compound of formula

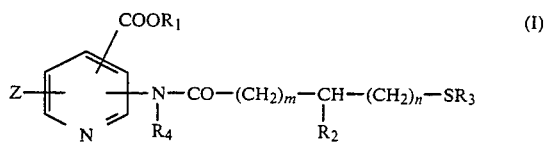

where

Z is hydrogen, alkyl having from 1 to 3 carbon atoms, halogen or alkoxy having from 1 to 3 carbon atoms;

$R_1$ is hydrogen, alkyl having from 1 to 6 carbon atoms, aryl alkyl having from 7 to 12 carbon atoms, aryl having 6 carbon atoms;

m and n are an integer of from 0 to 4 each provided, however, that m+n is lower than 5;

$R_2$ is hydrogen, alkyl having from 1 to 6 carbon atoms or arylalkyl having from 7 to 12 carbon atoms;

$R_3$ is hydrogen or acyl of a carboxylic acid having from 1 to 8 carbon atoms;

$R_4$ is hydrogen or alkyl having from 1 to 3 carbon atoms;

and pharmaceutically acceptable salts thereof with organic or inorganic acids.

2. A compound according to claim 1, wherein Z is hydrogen, $R_1$ is an alkyl having from 1 to 3 carbon atoms, $R_2$ is hydrogen, methyl or benzyl, $R_3$ is acetyl or benzoyl, $R_4$ is hydrogen or methyl, m is 0 and n is 1; and pharmaceutically acceptable salts thereof with organic or inorganic acids.

3. Pharmaceutical composition containing a compound of formula

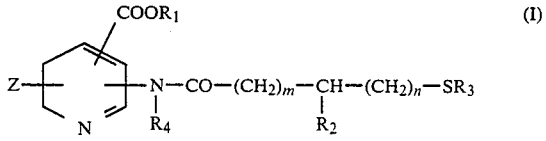

where

Z is hydrogen, alkyl having 1 to 3 carbon atoms, halogen or alkoxy having from 1 to 3 carbon atoms;

$R_1$ is hydrogen, alkyl having from 1 to 6 carbon atoms, aryl alkyl having from 7 to 12 carbon atoms, aryl having 6 carbon atoms;

m and n are an integer of from 0 to 4 each provided, however, that m+n is lower than 5;

$R_2$ is hydrogen, alkyl having from 1 to 6 carbon atoms or aryl alkyl having from 7 to 12 carbon atoms;

$R_3$ is hydrogen or acyl of a carboxylic acid having from 1 to 8 carbon atoms;

$R_4$ is hydrogen or alkyl having from 1 to 3 carbon atoms;

or a pharmaceutically acceptable salt thereof with organic or inorganic acids and a carrier, the amount of the compound of formula (I) being effective to inhibit enkephalinase.

4. Pharmaceutical composition according to claim 3, characterized in that Z is hydrogen, R1 is an alkyl having from 1 to 3 carbon atoms, R2 is hydrogen, methyl or benzyl, R3 is acetyl or benzoyl, R4 is hydrogen or methyl, m is 0 and n is 1.

5. A composition according to claim 3 containing 30 to 300 mg of the compound of formula (I), calculated as the free base.

6. A composition according to claim 4 containing 30 to 300 mg of the compound of formula (I), calculated as the free base.

7. A method of inhibiting enkephalinase comprising administering to an individual in need of such an inhibitor an amount of a compound of claim 1 effective for such purpose.

8. A method according to claim 7 where there is administered a dosage of 60 mg to 1 gram per day.

9. A method of inhibiting dipeptidyl carboxy peptidase comprising administering to an individual in need of such an inhibitor an amount of a compound of claim 1 effective to such purpose.

10. A method of inhibiting enkephalinase comprising administering to an individual in need of such an inhibitor an amount of a compound of claim 2 effective for such purpose.

11. A method according to claim 10 wherein there is administered a dosage of 60 mg to 1 gram per day.

12. A method of inhibiting dipeptidyl carboxy peptidase comprising administering to an individual in need of such an inhibitor an amount of a compound of claim 2 effective for such purpose.

* * * * *